(12) United States Patent
Horng et al.

(10) Patent No.: US 8,855,732 B2
(45) Date of Patent: Oct. 7, 2014

(54) NON-INVASIVE APPARATUS AND METHOD FOR MEASURING HUMAN METABOLIC CONDITIONS

(75) Inventors: Jenq-Ruey Horng, Tainan County (TW); Shoko Nioka, Philadelphia, PA (US); Chi-Jo Wang, Tainan County (TW); Chih-Chieh Kang, Tainan County (TW); Juing-Shian Chiou, Tainan County (TW); Shih-Chung Chen, Tainan County (TW); Chih-Kuo Liang, Tainan County (TW); Ching-Lung Chu, Tainan County (TW); Hung-Chi Yang, Tainan County (TW); Lian-Jou Tsai, Tainan County (TW); Tsung-Fu Jeng, Tainan County (TW)

(73) Assignee: Southern Taiwan University, Tainan County (TW)

( * ) Notice: Subject to any disclaimer, the term of this patent is extended or adjusted under 35 U.S.C. 154(b) by 891 days.

(21) Appl. No.: 13/028,359

(22) Filed: Feb. 16, 2011

(65) Prior Publication Data
US 2012/0209092 A1 Aug. 16, 2012

(51) Int. Cl.
*A61B 5/1455* (2006.01)
*A61B 5/00* (2006.01)

(52) U.S. Cl.
CPC .............. *A61B 5/0071* (2013.01); *A61B 5/4552* (2013.01); *A61B 5/682* (2013.01); *A61B 5/1455* (2013.01)

USPC ............................................ 600/310; 600/322

(58) Field of Classification Search
USPC .......................... 600/310, 322, 323, 473, 476
See application file for complete search history.

(56) References Cited

U.S. PATENT DOCUMENTS

| 6,912,412 | B2 * | 6/2005 | Georgakoudi et al. | 600/310 |
|---|---|---|---|---|
| 7,130,672 | B2 * | 10/2006 | Pewzner et al. | 600/310 |
| 2002/0016534 | A1 * | 2/2002 | Trepagnier et al. | 600/316 |

* cited by examiner

*Primary Examiner* — Eric Winakur
(74) *Attorney, Agent, or Firm* — Rosenberg, Klein & Lee

(57) ABSTRACT

In a non-invasive human metabolic condition measuring apparatus and method, a micro-light source emits an incident light having a wavelength from 329 nm to 473 nm to trigger a mitochondrial metabolite of a human mucosa tissue, and the metabolite is excited to generate a fluorescent signal having a wavelength from 405 nm to 572 nm, and the fluorescent signal is filtered by an optical filter, received by a micro receiver, and amplified by an amplification circuit sequentially, and then a filter circuit and an analog/digital conversion circuit of a microprocessing unit are provided for filtering and performing an analog/digital signal conversion respectively, so that the metabolite content can be calculated by the computation to provide human metabolic conditions, and a combination of micro components and circuits is used for miniaturizing the apparatus to provide a convenient carry of the apparatus.

19 Claims, 9 Drawing Sheets

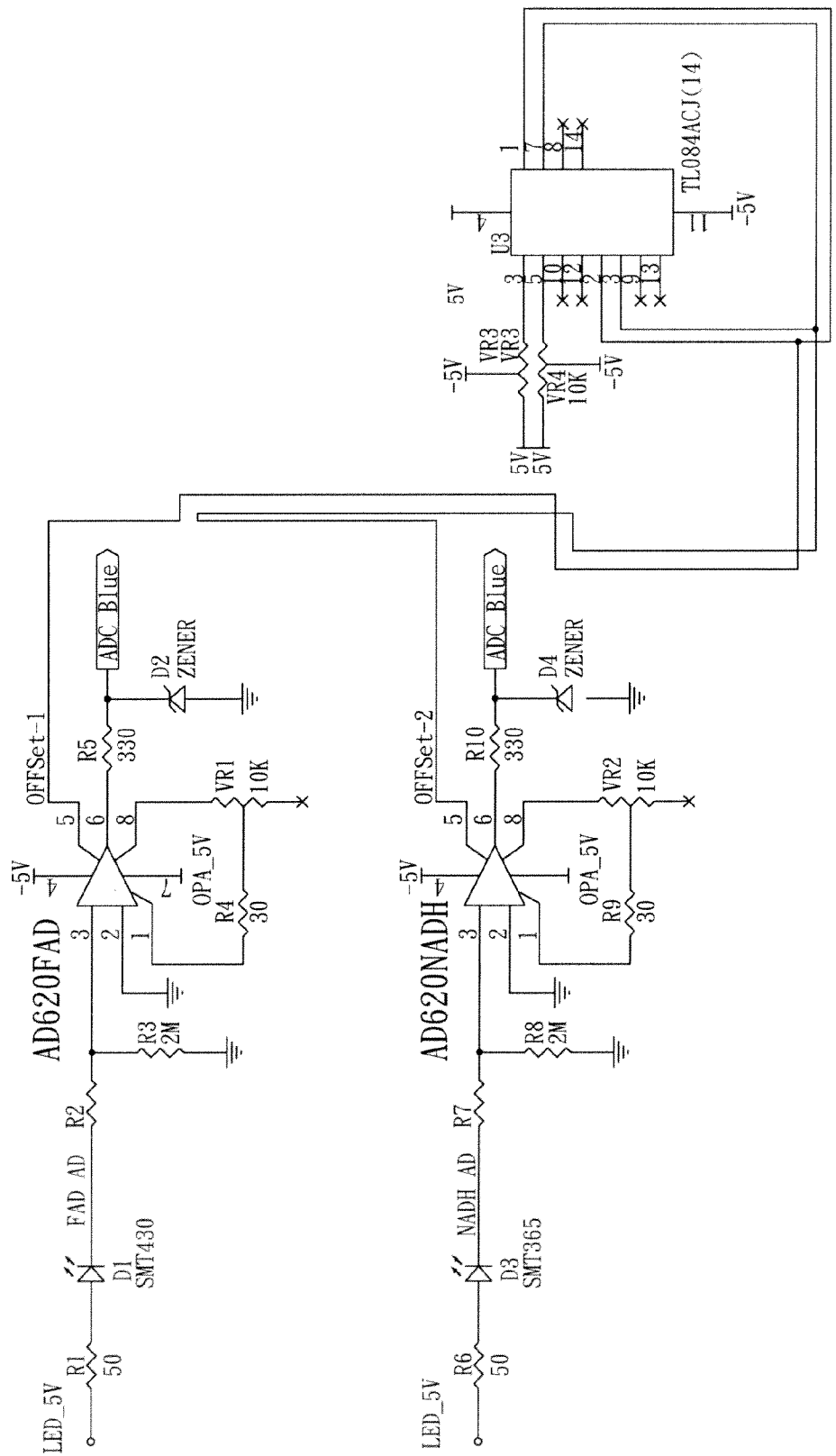
F I G . 3-A

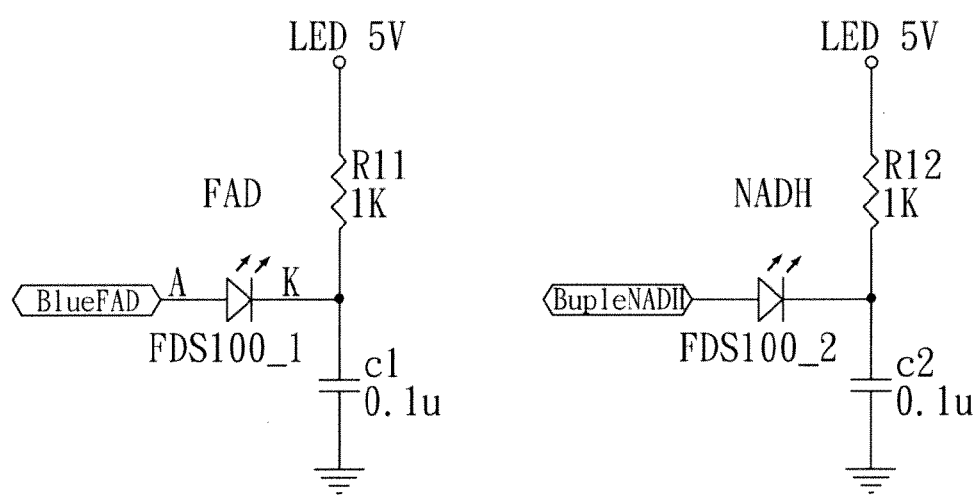
FIG. 3-B

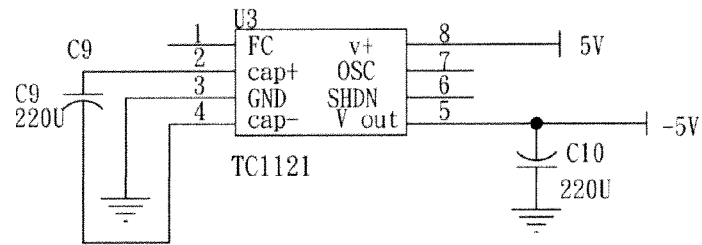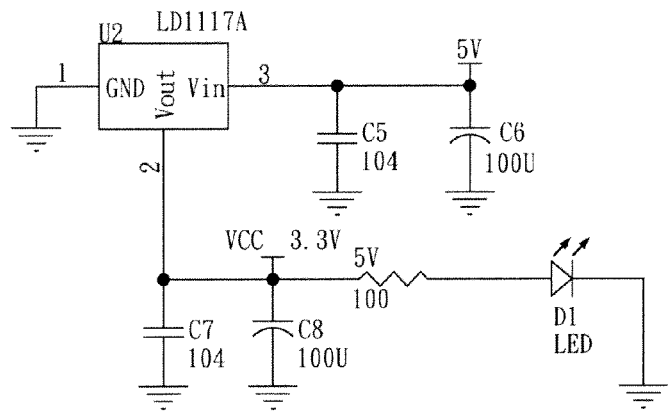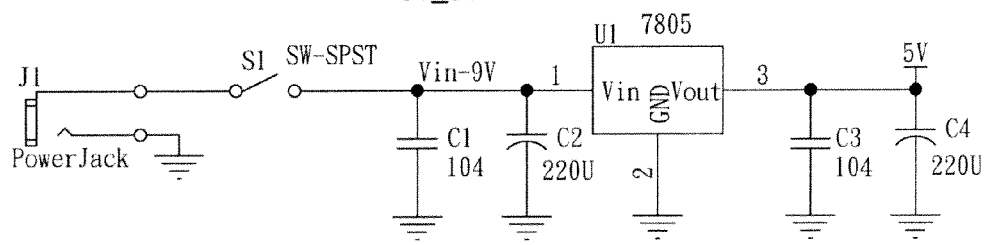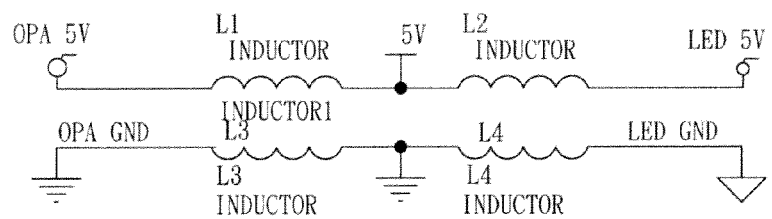
FIG.4-A

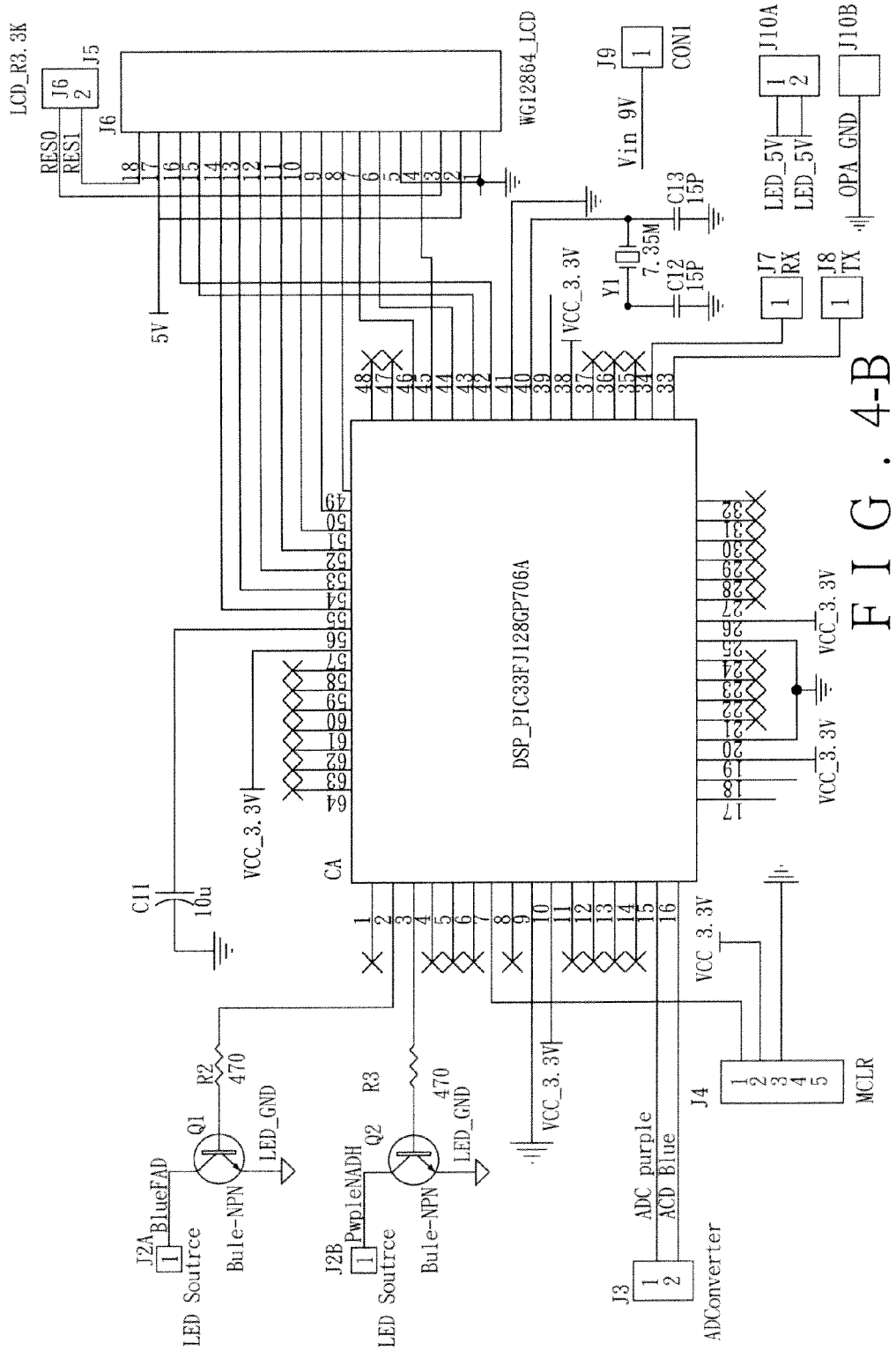
FIG. 4-B

US 8,855,732 B2

NON-INVASIVE APPARATUS AND METHOD FOR MEASURING HUMAN METABOLIC CONDITIONS

BACKGROUND OF THE INVENTION

1. Field of the Invention

The present invention relates to a non-invasive human metabolic condition measuring apparatus and method, and more particularly to a non-invasive apparatus and method using a combination of micro components and circuits to detect the content of a mitochondrial metabolite of a human mucosa tissue to determine metabolic conditions.

2. Description of the Related Art

Three major nutrients of food including sugar, fat and protein can be hydrolyzed in a living body to form monosaccharide, fatty acid and amino acid which are entered into cells, and a series of chemical reactions will occur in mitochondrion to produce adenosine triphosphate (ATP) which will be outputted together with energy, and thus the three major nutrients become an energy source of a living body.

The chemical reactions taken place in the mitochondrion are mainly completed by enzymes of a tricarboxylic acid cycle (TCA cycle), and the enzymes can further decompose acetyl-CoA metabolically produced from sugar, fat and protein into reduced molecules such as carbon dioxide, nicotinamide adenine dinucleotide (NADH) and flavin adenosine dinucleotide (FADH2). Respiratory enzyme complexes on an inner membrane of the mitochondrion oxidize the reduced molecules including NADH and FADH2 by oxygen molecules through electron transport chains into $NADH^+$ and FAD, while producing water and ATP, and ATP is formed by adenine, α-D-ribose and α, β, γ—phosphates, and energy contained in ATP is stored in β and γ—phosphates bonds of the three phosphate molecules, such that when ATP is hydrolyzed to form Adenosine 5'-diphosphate (ADP) or Adenosine 5'-monophosphate (AMP), the energy will be released [Refer to Science Monthly, Issue 312, December 1995, "Mitochondrion Aging Theory and Discussions on Disease and Aging of Mitochondrion" by Cheng-yoong Pang and Yau-huei Wei].

NADH and FAD are products of nutrient metabolism, and NADH and FAD are excited by an ultraviolet light or a blue light with a short wavelength to produce a fluorescent light, and the structure of human tissues is changed during a carcinogenesis process. More significantly, the metabolism of cancer cells is faster than the metabolism of normal cells, so that the quantity of NADH is increased to give an abnormal ratio of NADH and FAD and produce a fluorescent spectrum different from those of the normal tissues.

In present applications of clinical medicines, the fluorescent spectra of NADH and FAD are used in the areas of testing an early-stage cancer, a nutrient metabolic condition of diabetes patients, and a metabolic condition of new-born babies, etc as mentioned in Science Development, Issue 451, July 2010, "Testing Principle of Fluorescence Technology" of Volume "Bio-medical Electronics", but the intensity of the fluorescent light produced by NADH and FAD is very low, so that general testing procedure by means of the fluorescence technology us an invasive testing procedure that cuts tissue cells or draws blood from an examinee's body and performs the test outside the examinee's body. Such invasive testing method always causes a patent's fear or even infections to a patient with a weak immunity system. Some laboratories are using large non-invasive testing instruments for experiments and researches, but the large non-invasive testing equipments not only have the disadvantages of a large size and an inconvenient carry, but also incur a high cost, and thus they are not suitable for regular tests taken by patients at home.

SUMMARY OF THE INVENTION

In view of the aforementioned shortcomings, the inventor of the present invention based on years of experience in the related industry to conduct extensive researches and experiments, and finally developed a non-invasive human metabolic condition measuring apparatus and method that allow the aforementioned fluorescent light to pass through human mucosa tissues, since the thickness of human mucosa tissues is much thinner than human skin, and the non-invasive method is used for measuring a mitochondrion metabolite content of the human mucosa tissues to determine the metabolic conditions. A testing apparatus with a combination of micro components and circuits is developed to miniaturize the testing apparatus and provide a convenient carry and use. The testing apparatus comprises at least one micro-light source, at least one optical filter, at least one micro receiver, an amplification circuit and a microprocessing unit, and the microprocessing unit further includes a filter circuit and an analog/digital conversion circuit.

The operation procedure is described further as follows:

In Step (a), the micro-light source emits an incident light having a wavelength from 329 nm to 473 nm. In Step (b), the incident light triggers a mitochondrial metabolite of a human mucosa tissue, such that the metabolite generates a fluorescent signal having a wavelength from 405 nm to 572 nm. In Step (c), the fluorescent signal is passed through an optical filter and transmitted to a micro receiver. In Step (d), the fluorescent signal is amplified. In Step (e), the amplified fluorescent signal is filtered, processed by an analog/digital signal conversion, and computed to obtain a computational value related to the mitochondrial metabolite.

In Step (a), a micro-light source emits an ultraviolet light having a wavelength from 329 nm to 403 nm, and the metabolite is FAD, and the FAD absorbs the ultraviolet light to generate a fluorescent signal having a wavelength from 405 nm to 495 nm, and the computational value calculated by the microprocessing unit in Step (e) is a FAD content.

In Step (a), a micro-light source emits a blue light having a wavelength from 387 nm to 473 nm, and the metabolite is NADH, and the NADH absorbs the blue light to generate a fluorescent signal having a wavelength from 468 nm to 572 nm, and the computational value calculated by the microprocessing unit in Step (e) is a NADH content.

In Step (a), two micro-light sources sequentially emit an ultraviolet light having a wavelength from 329 nm to 403 nm and a blue light having a wavelength from 387 nm to 473 nm, and the metabolites are FAD and NADH, and the FAD absorbs the ultraviolet light to generate a fluorescent signal having a wavelength from 405 nm to 495 nm, and the NADH absorbs the blue light to generate a fluorescent signal having a wavelength from 468 nm to 572 nm, and the computational values computed by the microprocessing unit in Step (e) are a FAD content, a NADH content and a ratio of the FAD content and the NADH content.

In Step (e), the microprocessing unit compares the computational value with a comparing value in a database, so that the computational value further includes a comparison result, and the computational value is outputted by a first output unit.

In Step (e), the microprocessing unit converts the computational value into an electric signal, and the electric signal is outputted by a signal transmitting module, received by a signal receiving module, and modulated by a control unit to produce the computational value, and the computational value is outputted by a second output unit and provided for a user's near-end monitoring or for a medical professional's instant remote monitoring.

The present invention further comprises a casing, wherein the aforementioned micro-light sources and micro receivers are combined with the casing, and the optical filter is installed onto the micro receiver, and the casing further includes a handle extended from the casing and provided for facilitating a user's grip and use.

Further, the micro-light source is a light emitting diode (LED) or a combination of a laser light source and a diffuser. The LED or laser light source has the advantage of a small size, so that the testing apparatus of the present invention can also have the advantage of a small size.

Further, the microprocessing unit is a microcontroller, an embedded system chip or a FPGA chip that also has the advantage of a small size and can be used for the a portable testing apparatus.

In summation, the present invention has the following advantages and effects:

1. A non-invasive method is used for measuring human metabolic conditions to improve the examinee's willingness of taking the test and make the testing procedure quicker and more convenient.

2. The scope of application is broad, and the present invention can be used in many different areas including a non-invasive blood sugar meter, a quick test for cancer treatments, a metabolic test for a new-born baby and a preliminary oral cavity test for pathological changes.

3. The measuring apparatus is comprised of micro components and circuits, such that the measuring apparatus can be miniaturized to provide a convenient carry and use.

BRIEF DESCRIPTION OF THE DRAWINGS

FIG. 3-A and FIG. 3-B are schematic circuit diagrams of a non-invasive human metabolic condition measuring apparatus in accordance with the present invention;

FIG. 4-A and FIG. 4-B are schematic circuit diagrams of a non-invasive human metabolic condition measuring apparatus in accordance with the present invention;

DETAILED DESCRIPTION OF THE PREFERRED EMBODIMENTS

The technical characteristics, effects and advantages of the present invention will be apparent with the detailed description of preferred embodiment together with the illustration of related drawings as follows.

Figure 1:
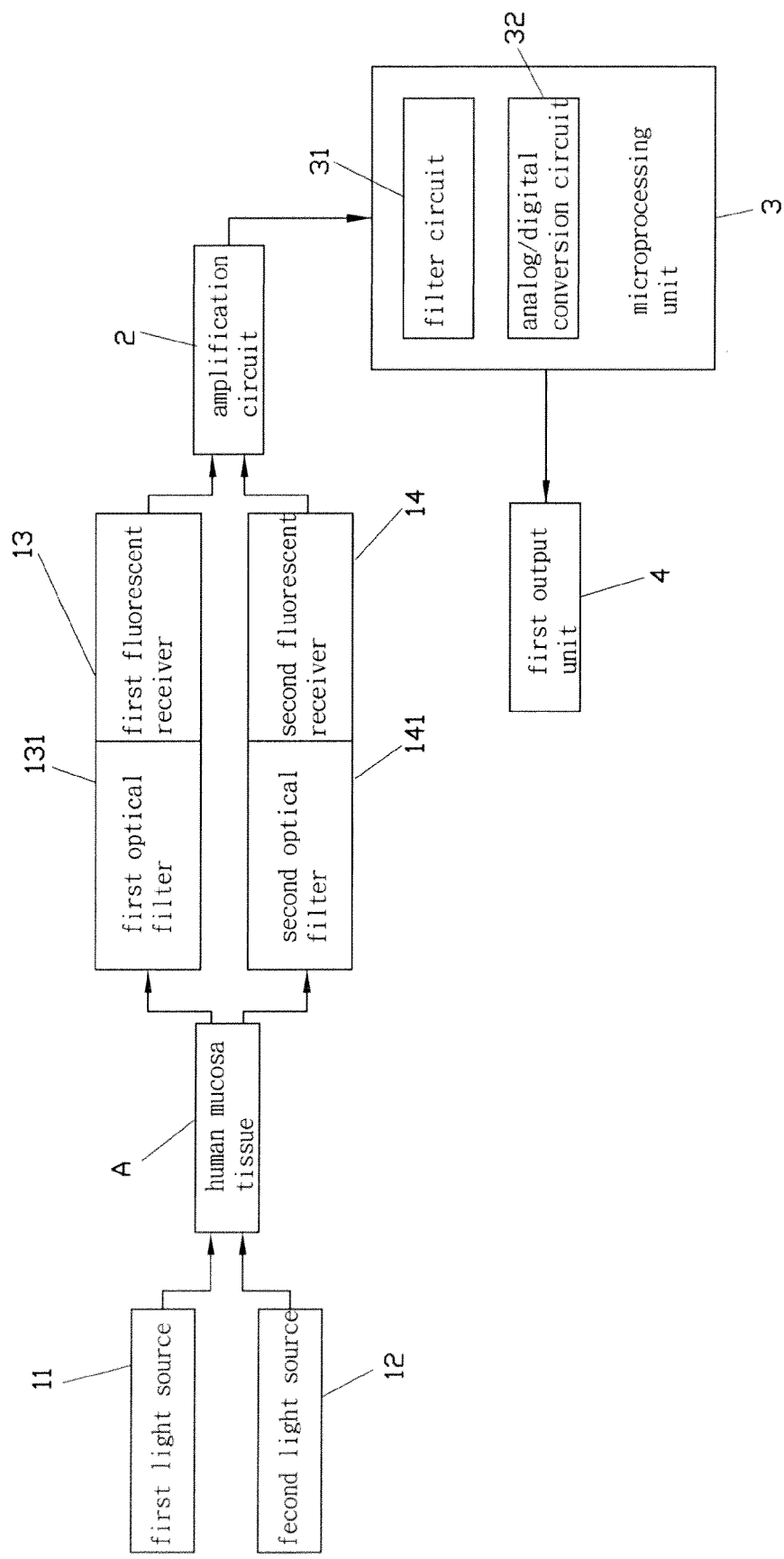
FIG. 1 is a block diagram showing a testing procedure and a relation of corresponding components of a non-invasive human metabolic condition measuring apparatus in accordance with the present invention.
Figure 2:
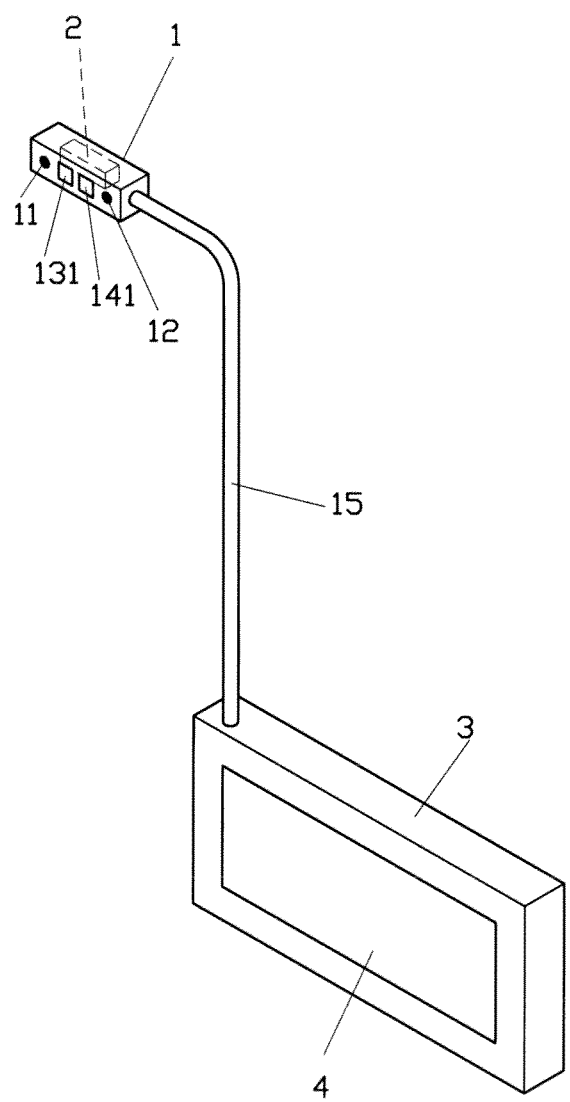
FIG. 2 is a perspective view of a non-invasive human metabolic condition measuring apparatus in accordance with the present invention.

With reference to FIGS. 1 and 2 for a non-invasive human metabolic condition measuring apparatus and method in accordance with a first preferred embodiment of the present invention, the apparatus comprises a casing (which is a small detection head 1) having two micro-light sources and two micro receivers installed thereon, wherein each of the micro-light sources of this preferred embodiment is a light emitting diode (LED), and the LED has the advantage of a small size that can further miniaturize the detection head 1. Besides LED, each of the micro-light sources can also be composed of a laser light source and a diffuser. Since laser light is a point light source, the diffuser can be used for diverging the laser light of the laser light source, and the laser light source also has the advantage of a small size to miniaturize the detection head 1 and divide each of the micro-light sources into a first light source 11 and a second light source 12 and each of the micro receivers into a first fluorescent receiver 13 and a second fluorescent receiver 14, and a handle 15 is extended from the detection head 1 and provided for facilitating a user's grip, and the first fluorescent receiver 13 and the second fluorescent receiver 14 include a first optical filter 131 and a second optical filter 141 respectively. An amplification circuit 2 is electrically coupled to the first fluorescent receiver 13 and the second fluorescent receiver 14 and combined into the detection head 1. A microprocessing unit 3 is electrically coupled to the amplification circuit 2, and the microprocessing unit 3 includes a filter circuit 31 and an analog/digital conversion circuit 32, wherein the microprocessing unit 3 can be a microcontroller, an embedded system chip or a FPGA chip that also has the advantage of a small size. A first output unit 4 is electrically coupled to the microprocessing unit 3 and connected to the handle 15, the miniaturized detection head 1, the microprocessing unit 3 and other circuit components to provide a portable testing apparatus.

With reference to FIGS. 3-A, 3-B, 4-A and 4-B for schematic circuit diagrams of the present invention, the connecting relation between circuits of the present invention is illustrated.

Figure 5:
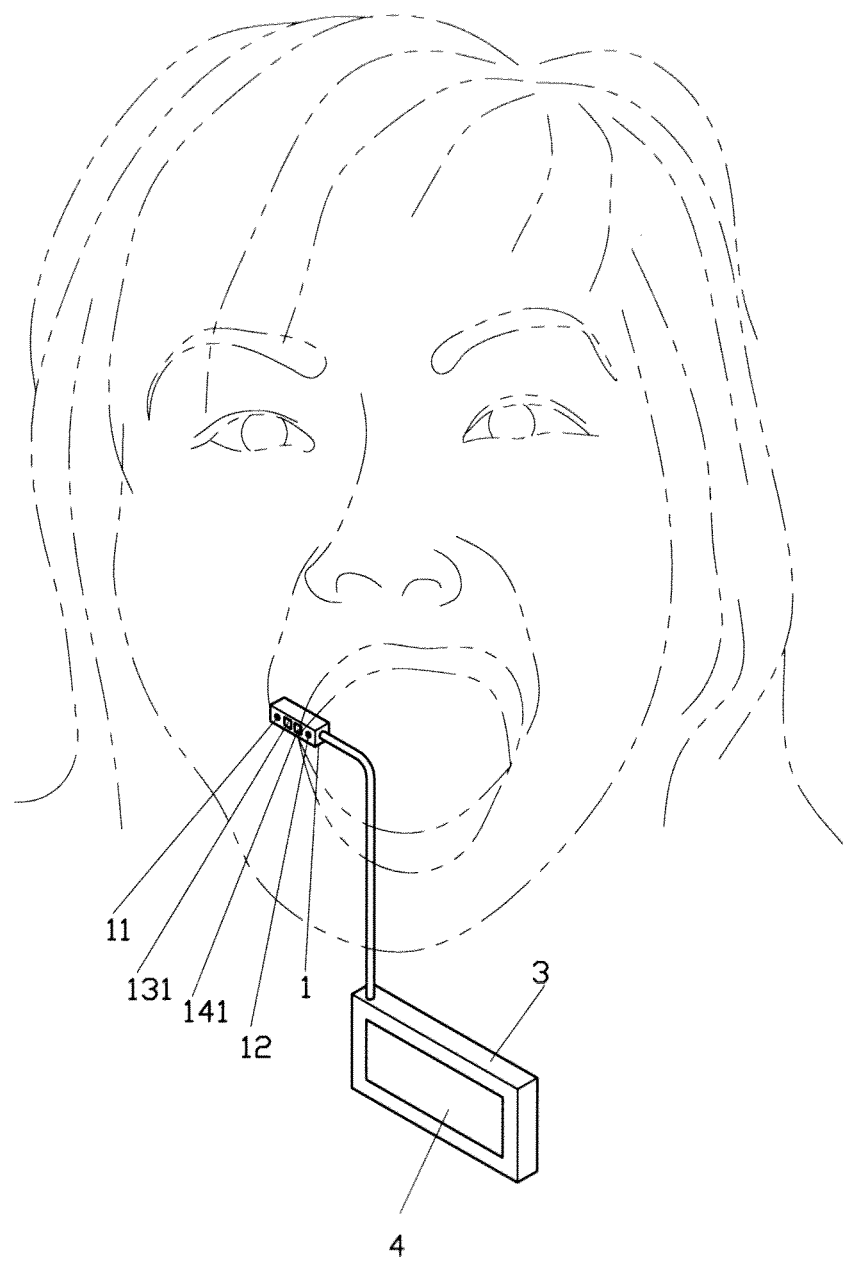
FIG. 5 is a schematic view of applying the present invention in an oral mucosa test.

With reference to FIGS. 1 and 5, the operation procedure is described as follows:

(a) The first light source 11 emits an ultraviolet light having a wavelength from 329 nm to 403 nm, and the second light source 12 emits a blue light having a wavelength from 387 nm to 473 nm. More precisely, the first light source 11 emits an ultraviolet light with a wavelength of 365 nm, and the second light source 12 emits a blue light with a wavelength of 430 nm.

(b) The detection head 1 is aligned precisely with a human mucosa tissue A, preferably an oral mucosa tissue. Since it is more convenient to detect the oral mucosa tissue and sequentially switch to the first light source 11 and second light source 12, the ultraviolet light and the blue light can be projected to the human mucosa tissue A sequentially, and the FAD in the mitochondrion of the human mucosa tissue A absorbs the ultraviolet light to generate a fluorescent signal having a wavelength from 405 nm to 495 nm, and the NADH in the mitochondrion of the human mucosa tissue A absorbs the blue light to generate a fluorescent signal having a wavelength from 468 nm to 572 nm. In correspondence with the aforementioned ultraviolet light with a wavelength of 365 nm and the aforementioned blue light with a wavelength of 430 nm, the FAD and NADH can generate the fluorescent signals with wavelengths of 450 nm and 520 nm respectively.

(c) The fluorescent signal is passed through the first optical filter 131 and the second optical filter 141 to filter any optical signals other than the fluorescent signal, since the intensity of the fluorescent signal is weaker and any interference of noises should be avoided. Therefore, it is necessary to filter unnecessary noises, and the first fluorescent receiver 13 and the second fluorescent receiver 14 can be used for receiving the fluorescent signals of the two wavelengths.

(d) The amplification circuit 2 is provided for amplifying the fluorescent signals received by the first fluorescent receiver 13 and the second fluorescent receiver 14 to facilitate the reading and determination made by the microprocessing unit 3.

(e) The microprocessing unit 3 receives and filters the fluorescent signal, and performs an analog/digital signal conversion to the fluorescent signal by the filter circuit 31 and the analog/digital conversion circuit 32, and then the microprocessing unit 3 computes a computational value according to the intensity of fluorescent signals of the two wavelengths, and the computational value includes a numeric value of the FAD content in the mitochondrion of the human mucosa tissue, a numeric value of the NADH content in the mitochondrion of the human mucosa tissue, and a ratio of the aforementioned two numeric values, and the first output unit 4 outputs the computational value, and the first output unit 4 preferably a display screen provides a convenient observation of a change of the computational values. Therefore, the relation of the FAD and the NADH can be used for determining human metabolic conditions.

Figure 6:
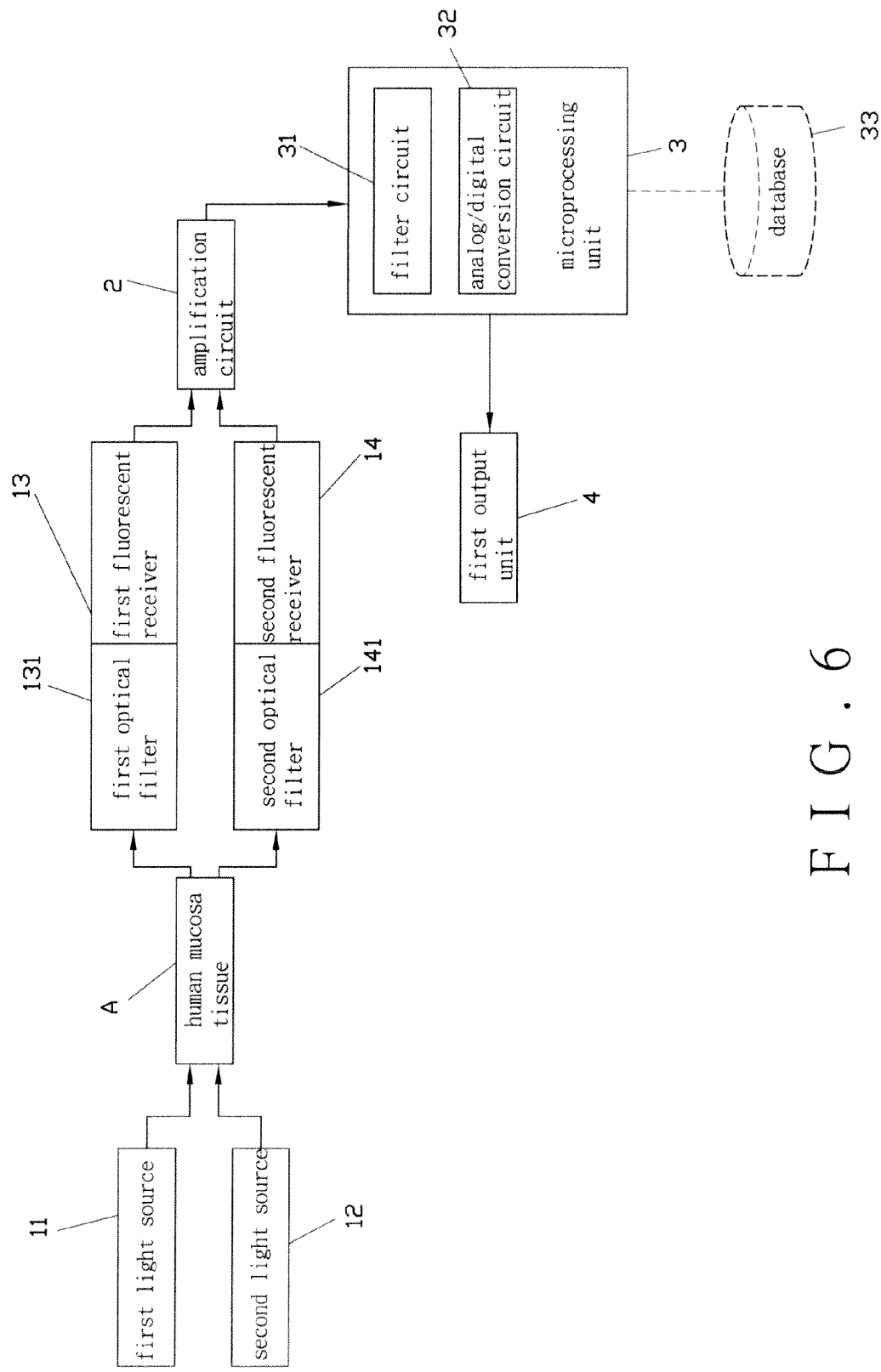
FIG. 6 is a block diagram showing a testing procedure and a relation of corresponding components of a microprocessing unit of a non-invasive human metabolic condition measuring apparatus added with a database in accordance with the present invention.

With reference to FIG. 6 for a second preferred embodiment of the present invention, the difference of the second preferred embodiment from the first preferred embodiment resides on that the microprocessing unit 3 of the second preferred embodiment further includes a database 33, and the database 33 stores a comparing value for comparing the numeric values of the FAD content, the NADH content and the ratio of the two numeric values to produce a comparison result, and the first output unit 4 is provided for outputting the comparison result. Now, the first output unit 4 can be a display screen for outputting the comparison result directly, or a buzzer for producing a warning sound if the numeric value of the FAD content, the numeric value of the NADH content, or the ratio of the two numeric values exceeding or falling below the comparing value.

Figure 7:
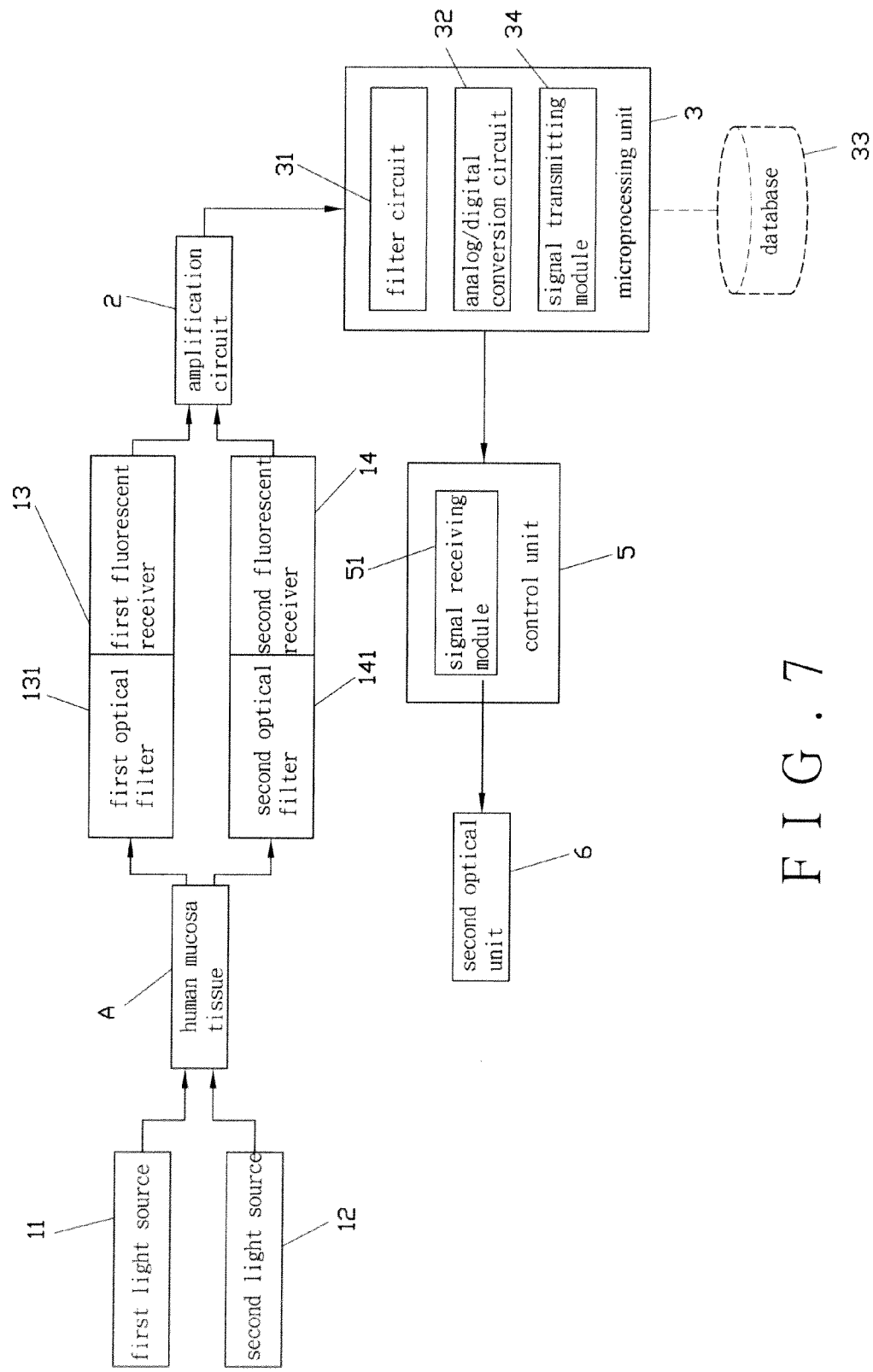
FIG. 7 is a block diagram showing a testing procedure and a relation of corresponding components of a non-invasive human metabolic condition measuring apparatus applied in a remote healthcare system in accordance with the present invention.

With reference to FIG. 7 for a third preferred embodiment of the present invention, the difference of the third preferred embodiment from the first and second preferred embodiments resides on that the first output unit 4 is used for a near monitoring. Now, the microprocessing unit 3 includes a signal transmitting module 34 and converts the computational value into an electric signal, and the signal transmitting module 34 outputs the electric signal, and then a signal receiving module 51 of a control unit 5 receives the electric signal, and the control unit 5 demodulates the electric signal to produce the computational value, and a second output unit 6 outputs the computational value, such that a medical professional can use the computational value for an instant remote monitoring.

The applications of the present invention are described briefly as follows:

Self Test for Diabetes Patient: Examinees have to pierce a finger to collect drops of blood for measuring the blood sugar level by a conventional blood sugar meter, but some examinees do not take the measurement daily because of the pain and inconvenience, and thus affecting the effective blood sugar control. The present invention adopting a non-invasive testing method can improve the examinee's willingness of taking the test. In addition, the testing procedure is quick and convenient, and thus further improving the frequency of using the apparatus of the invention daily by diabetes patients.

Quick Test for Cancer Treatment Effect: In cancer treatments through a targeted drug therapy, and a radiation therapy, it takes some time before the treatment effect of the radiation therapy can be known. In fact, the human metabolism starts changing on the next day after a patient takes the medicine or radiation therapy. If the measuring apparatus of the present invention is used for the test, the treatment effect can be known the next day after the treatment is taken, and thus significantly improving the medical treatment process of cancer patients.

Metabolic Test for New-born Babies: The numeric value of metabolism of a new-born baby can be measured to detect whether or not any abnormal condition exists immediately after the baby was born.

Detection of Early-stage Pathological Change of Oral Cavity: There are many oral cancer patients in Taiwan, but patients always seek for medical help after the oral cells of the patient sense abnormality. As to dentistry, the measuring apparatus of the present invention can be used in regular oral examinations of the high risk group detect abnormal changes of oral cells at an early stage.

What is claimed is:

1. A portable non-invasive human metabolic condition measuring apparatus, comprising:
   a miniature casing adapted for insertion into a body cavity of a patient or placement adjacent the patient's body;
   at least one micro-light source located within said miniature casing, for emitting an incident light having a wavelength from 329 nm to 473 nm to excite a metabolite to emit a fluorescent signal having a wavelength from 405 nm to 572 nm;
   at least one optical filter, located within said miniature casing adjacent the micro-light source, for filtering an optical signal other than the fluorescent signal;
   at least one micro receiver, located within said miniature casing adjacent the micro-light source, for receiving a fluorescent signal passed through the optical filter;
   an amplification circuit, located within said miniature casing and electrically coupled to the micro receiver, for amplifying the fluorescent signal;
   a microprocessing unit, positioned external said miniature casing and electrically coupled to the amplification circuit, and including a filter circuit and an analog/digital conversion circuit, for filtering the amplified fluorescent signal, performing an analog/digital signal conversion, and calculating a computational value related to the metabolite by a computational processing; and
   an elongated handle for structurally and electrically coupling said microprocessing unit to said miniature casing, said elongated handle adapted to be grasped by a hand of a user for manipulating the miniature casing.

2. The portable non-invasive human metabolic condition measuring apparatus of claim 1, comprising one of the micro-light sources and one of the micro receivers, wherein the micro-light source emits an ultraviolet light having a wavelength from 329 nm to 403 nm, and the metabolite is FAD, and the FAD absorbs the ultraviolet light to generate a fluorescent signal having a wavelength from 405 nm to 495 nm, and the computational value is a FAD content.

3. The portable non-invasive human metabolic condition measuring apparatus of claim 1, comprising one of the micro-light sources and one of the micro receivers, wherein the micro-light source emits a blue light having a wavelength from 387 nm to 473 nm, and the metabolite is NADH, and the NADH absorbs the blue light to generate a fluorescent signal having a wavelength from 468 nm to 572 nm, and the computational value is a NADH content.

4. The portable non-invasive human metabolic condition measuring apparatus of claim 1, comprising two of the micro-light sources and two of the micro receivers, wherein each micro-light source sequentially emits an ultraviolet light having a wavelength from 329 nm to 403 nm and a blue light having a wavelength from 387 nm to 473 nm, and the metabolites are FAD and NADH, and the FAD absorbs the ultraviolet light to generate a fluorescent signal having a wavelength from 405 nm to 495 nm, and the NADH absorbs the blue light to generate a fluorescent signal having a wavelength from 468 nm to 572 nm, and the computational values are a FAD content, a NADH content, and a ratio of the FAD content and the NADH content.

5. The portable non-invasive human metabolic condition measuring apparatus of claim 1, wherein the microprocessing unit further includes a database, and stores a comparing value, for comparing the computational value, such that the computational value further includes a comparison result.

6. The portable non-invasive human metabolic condition measuring apparatus of claim 1, further comprising a first output unit electrically coupled to the microprocessing unit for outputting the computational value.

7. The portable non-invasive human metabolic condition measuring apparatus of claim 1, wherein the microprocessing unit converts the computational value into an electric signal, and further includes a signal transmitting module for transmitting the electric signal, and a control unit having a signal receiving module for receiving the electric signal, and then the control unit modulates the electric signal to produce the computational value.

8. The portable non-invasive human metabolic condition measuring apparatus of claim 7, further comprising a second output unit electrically coupled to the control unit for outputting the computational value.

9. The portable non-invasive human metabolic condition measuring apparatus of claim 1, wherein the micro-light source is a light emitting diode (LED).

10. The portable non-invasive human metabolic condition measuring apparatus of claim 1, wherein the micro-light source is comprised of a laser light source and a diffuser.

11. The portable non-invasive human metabolic condition measuring apparatus of claim 1, wherein the microprocessing unit is a microcontroller, an embedded system chip or a FPGA chip.

12. A non-invasive human metabolic condition measuring method, comprising:
(a) providing a measuring apparatus comprising a miniature casing adapted for insertion into a body cavity or a patient or placement adjacent the patient's body, a micro-light source within said miniature casing for emitting an incident light having a wavelength from 329 nm to 473 nm, and an elongated handle structurally and electrically coupling said miniature casing to a microprocessing unit located external said miniature casing;
(b) irradiating a mitochondrial metabolite of a human mucosa tissue with the incident light to excite the metabolite to emit a fluorescent signal having a wavelength from 405 nm to 572 nm;
(c) passing the fluorescent signal through an optical filter to a micro receiver located adjacent said micro-light source within said miniature casing;
(d) amplifying the fluorescent signal by an amplification circuit within said miniature casing;
(e) transmitting the amplified fluorescent signal to said microprocessing unit; and
(f) filtering the amplified fluorescent signal, and performing an analog/digital signal conversion and computation of the amplified fluorescent signal to obtain a computational value related to the mitochondrial metabolite.

13. The non-invasive human metabolic condition measuring method of claim 12, wherein the step (b) includes emitting an ultraviolet light having a wavelength from 329 nm to 403 nm by a micro-light source, and the metabolite is FAD, and a fluorescent signal having a wavelength from 405 nm to 495 nm is generated after the FAD absorbs the ultraviolet light, and the computational value computed by the microprocessing unit in the step (e) is a FAD content.

14. The non-invasive human metabolic condition measuring method of claim 12, wherein the step (b) includes emitting a blue light having a wavelength from 387 nm to 473 nm by a micro-light source, and the metabolite is NADH, and a fluorescent signal having a wavelength from 468 nm to 572 nm is generated after the NADH absorbs the blue light, and the computational value computed by the microprocessing unit in the step (g) is a NADH content.

15. The non-invasive human metabolic condition measuring method of claim 14, wherein the step (b) includes transmitting an ultraviolet light having a wavelength from 329 nm to 403 nm and a blue light having a wavelength from 387 nm to 473 nm sequentially by two micro-light sources in step (b), and the metabolites are FAD and NADH, and a fluorescent signal having a wavelength from 405 nm to 495 nm is generated after the FAD absorbs the ultraviolet light, and a fluorescent signal having a wavelength from 468 nm to 572 nm after the NADH absorbs the blue light, and the computational values calculated by the microprocessing unit in the step (g) are a FAD content, a NADH content, and a ratio of the FAD content to the NADH content.

16. The non-invasive human metabolic condition measuring method of claim 12, wherein the microprocessing unit in the step (g) further compares the computational value and a comparing value in a database, such that the computational value further includes a comparison result.

17. The non-invasive human metabolic condition measuring method of claim 12, wherein the step (g) further outputs the computational value by a first output unit.

18. The non-invasive human metabolic condition measuring method of claim 12, wherein the microprocessing unit in the step (g) converts the computational value into an electric signal to be outputted by a signal transmitting module, received by a signal receiving module, and demodulated by a control unit into the computational value.

19. The non-invasive human metabolic condition measuring method of claim 18, further comprising the step of outputting the computational value by a second output unit.

* * * * *